United States Patent [19]

Doweyko et al.

[11] 4,360,677

[45] Nov. 23, 1982

[54] HERBICIDAL 2-(ALPHA-CHLOROMETHYLSULFONYL) PYRIDINE-1-OXIDES

[75] Inventors: Arthur M. P. Doweyko, Naugatuck; Richard R. Regis, Harwinton; Allyn R. Bell, Cheshire, all of Conn.

[73] Assignee: Uniroyal, Inc., New York, N.Y.

[21] Appl. No.: 77,431

[22] Filed: Sep. 20, 1979

[51] Int. Cl.$^3$ .......................................... C07D 213/64
[52] U.S. Cl. .................. 546/294; 546/270; 546/283; 71/94
[58] Field of Search .................. 546/294, 270; 71/94

[56] References Cited

U.S. PATENT DOCUMENTS

| | | | |
|---|---|---|---|
| 3,107,994 | 10/1963 | Rawlings et al. | 71/94 |
| 3,155,671 | 11/1964 | D'Amico | 260/290 |
| 3,772,307 | 11/1973 | Kaminsky et al. | 546/294 |
| 3,960,542 | 6/1976 | Plant et al. | 546/300 |
| 4,019,893 | 4/1977 | Plant et al. | 71/94 |
| 4,050,921 | 9/1977 | Plant et al. | 546/294 |

OTHER PUBLICATIONS

Walter et al., Liebig's Ann der Chemie, vol. 695, p.-77, (1966).

Shaw et al., Journal Amer. Chem. Soc. vol. 72, p. 4362 (1950).

*Primary Examiner*—Alan L. Rotman
*Attorney, Agent, or Firm*—James J. Long; Marvin Bressler

[57] ABSTRACT

Selective herbicidal 2-(alpha-chloromethylsulfonyl) pyridine-1-oxides, e.g., 2-(alpha-phenyl-alpha-chloromethylsulfonyl) pyridine-1-oxide controls weed grasses without injury to such crops as cucumber.

12 Claims, No Drawings

HERBICIDAL 2-(ALPHA-CHLOROMETHYLSULFONYL) PYRIDINE-1-OXIDES

This invention relates to 2-(alpha-chloromethylsulfonyl) pyridine-1-oxides, a herbicidal composition containing such oxide, and a method for herbicidal control of undesirable plant species using such oxide.

The herbicidal compounds of the invention have the formula

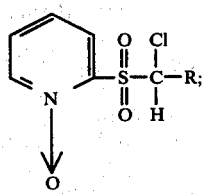

wherein R is selected from the group consisting of phenyl, phenyl substituted with at least one of the substituents $C_1$ to $C_8$ alkyl, $C_1$ to $C_8$ alkoxy, phenoxy, benzyloxy, halogen, trifluoromethyl, trichloromethyl, alkenyloxy, alkynyloxy, nitro, cyano, carboxy, carbalkoxy, carbamido, methylsulfonyl dioxymethylene, 2-naphthyl, and 2-(2',2'-dichloro-1'-methylcyclopropyl).

W. Walter et al., Liebig's Ann., 695, 77 (1966), disclose 2-(phenylmethylsulfinyl) pyridine 1-oxide (also called 2-benzylsulfinylpyridine 1-oxide) and 2-(phenylmethylsulfonyl) pyridine 1-oxide (also called 2-benzylsulfonylpyridine 1-oxide), but no utility for these chemicals is disclosed.

U.S. Pat. No. 3,107,994, Rawlings et al., Oct. 22, 1963, discloses certain herbicidal 2-(alkenylthio) pyridine 1-oxides, while U.S. Pat. No. 3,155,671, D'Amico, Nov. 3, 1964, discloses certain herbicidal benzyl 2-thiopyridine 1-oxides. U.S. Pat. Nos. 3,960,542 and 4,019,893, Plant et al., June 1, 1976 and Apr. 26, 1977 disclose certain 2-sulfinyl and 2-sulfonyl pyridine 1-oxides.

The state of the art is further illustrated by such references as E. Shaw et al., JACS 72, 4362 (1950) and U.S. Pat. No. 3,772,307, Kaminsky et al., Nov. 13, 1973.

The present 2-alpha-chloromethyl sulfonyl pyridine 1-oxide derivatives make possible markedly improved results, specifically in crop selectivity over various compounds of the prior art.

Weeds compete with crops for light, moisture, nutrients and space. Thus, weeds inhibit the production of foliage, fruit or seed of agricultural crops. The presence of weeds may also reduce the quality of the harvested crop and reduce harvesting efficiency. Weed control is essential for maximum production of many agronomic and horticultural crops including soybeans (*Glycine max* L.) peanuts (*Arachis hypogaea* L.) cotton (*Gossypium* sp.) sunflower (*Helianthus annuus* L.) and cucumber (*Cucumis sativus* L.)

In accordance with the invention, there are provided new herbicidally effective 2-(alpha-chloromethylsulfonyl) pyridine 1-oxides of the formula stated above.

The 2-(alpha-chloromethylsulfonyl) pyridine 1-oxide derivatives of the invention are useful for preemergence control of weeds, and are furthermore remarkable for their ability to selectively control weeds without injury to desirable crops. Excellent control of weeds such as switchgrass (*Panicum virgatum* L.), goosegrass (*Eleusine indica* (L.) Gaertn.), giant foxtail (*Setaria faberi* Herrm.), yellow foxtail *Setaria lutescens* (Weigel) Hubb.), green foxtail (*Setaria viridis* (L.) Beauv.) and barnyardgrass (*Echinochloa crusgalli* (L.) Beauv.) can be achieved with such chemicals as 2-[alpha-(2,5-dimethylphenyl)-alpha-chloromethylsulfonyl)] pyridine 1-oxide, without injury to such crops as cucumber (*Cucumis sativus* L.).

Surprisingly, the herein described 2-(alpha-chloromethylsulfonyl) pyridine 1-oxides are unexpectedly more selective herbicides than their corresponding precursors or corresponding alpha methyl substituted herbicides.

The procedures for using the present 2-(alpha-chloromethylsulfonyl) pyridine 1-oxide derivatives as herbicides may be in accordance with conventional agricultural practice. The chemicals are ordinarily applied as formulations containing a carrier and/or surface-active agent. The formulation may contain more than one of the described 2-(alpha-chloromethylsulfonyl) pyridine 1-oxide derivatives if desired; other active herbicides may be included in the formulation as well.

Thus, the chemical may be impregnated on finely divided or granular inorganic or organic carriers such as attapulgite clay, sand, vermiculite, corn cobs, activated carbon or other granular carriers known to the art. The impregnated granules may then be spread on the soil. Furthermore, the chemical may be formulated as a wettable powder by grinding it into a fine powder and mixing it with an inactive powdered carrier to which a surface active dispersing agent has been added. Typical powdered solid carriers are the various mineral silicates, e.g., mica, talc, pyrophyllite and clays. The wettable powder may then be dispersed in water and sprayed on the soil surface or weeds. Similarly, an emulsifiable concentrate may be prepared by dissolving the chemical in a solvent such as benzene, toluene, or other aliphatic or aromatic hydrocarbon to which a surface active dispersing agent has been added. The emulsifiable concentrate may then be dispersed in water and applied by spraying. Suitable surface active agents are well known to those skilled in the art and reference may be had to McCutcheon's Detergents and Emulsifiers, 1970, Allured Publishing Corp., Ridgewood, New Jersey; or Hoffman et al. U.S. Pat. Nos. 2,614,916, cols. 2 to 4 and 2,547,724, cols. 3 and 4, for example of appropriate surface active agents. The concentration of active chemical in the formulation may vary widely, e.g., from 1 to 95%. The concentration of active chemical in dispersions applied to the soil or foliage is almost invariably from 0.002% to 75%. The chemical is frequently applied at rates of 0.10 to 25 pounds per acre. For use as a preemergence herbicide, the chemical is applied to soil which contains weed and crop seed (either to the surface of the soil or incorporated into the upper one to three inches of soil).

The most suitable rate of application in any given case will depend on such factors as soil type, soil pH, soil organic matter content, the quantity and intensity of rainfall before and after treatment, the air and soil temperature, light intensity and light duration per day. All of these factors can have an influence on the efficacy of the chemicals for use as herbicides.

The herbicidal use may include selective weed control in crops such as cucumber, soybeans, cotton, and peanuts.

Compounds of the invention may be used for selective control of various grasses in diverse crops including Cucumber (*cucumis sativus* L.), alfalfa (*Medicago sativa* L.), cotton (*Gossypium* sp.), soybeans *Glycine max* (L.) Merr., peanuts (*Arachis hypogaea* L.), tomatoes (*Lycopersicon esculentum* Mill.) and tobacco (*Nicotiana tabacum* L.). Application may be in aqueous solutions or suspensions which may be sprayed onto the soil surface prior to weed and crop emergence and before or after the crop seed is sown. The soil may receive a shallow tilling (less than 3 inches) after application of the chemical, but this is not required as it is with some preemergence herbicides. The compounds of this invention may also be applied by broadcast of a granular formulation prior to weed and crop emergence.

Various weeds such as crabgrass *Digitaria ischaemum* (Schreb.) Muhl. may be controlled by postemergence application of compounds of this invention.

Compound of this invention may be added as a "tank mix" to other herbicide solutions so that the number of different weed species controlled in a single application will be increased. The formulations of invention compounds may also include other herbicides so that the spectrum of weeds controlled by spray or granular application may be increased.

The types of starting materials most generally employed in the preparation of these compounds are known and described in the literature. These parent 2-aryl-methylsulfonylpyridine-1-oxides are prepared by methods cited in U.S. Pat. No. 3,960,542. Their subsequent conversion to the title compounds (alpha-chloromethylsulfonyl)pyridine-1-oxides is carried out using a modification of a known procedure. (C. Y. Meyers, et al., *J. Org. Chem.*, 91, 7510 (1969); C. Y. Meyers, et al., *Tetrahedron Lett.*, 1105 (1974)).

The solvent, N,N-dimethylformamide, is used without drying. Sodium hydroxide (97–98%) is freshly ground to a powder before use, care being taken to avoid prolonged exposure to moisture. Temperature is generally maintained from −5° to +5° C., with reaction times between 25 and 35 min.

The synthesis of the 2-(alpha-aryl-alpha-chloromethylsulfonyl) pyridine-1-oxides and of 2-[alpha-(2',2'-dichloro-1'-methylcyclopropyl)-alpha-chloromethylsulfonyl] pyridine-1-oxide can be illustrated by the following examples:

EXAMPLE 1

2-(alpha-phenyl-alpha-chloromethylsulfonyl) pyridine-1-oxide

Carbon tetrachloride (3.1 g, 20 mmol) and freshly ground sodium hydroxide (1.0 g, 25 mmol) were placed in 25 ml of dimethylformamide. The mixture was cooled to 0° using an acetone-ice bath and while vigorously stirring, 2-(phenylmethylsulfonyl) pyridine-1-oxide (5.00 g, 20 mmol) was added in one portion. After 20 min. the mixture was poured into 300 ml of well-stirred water, resulting in a suspension of light tan precipitate.

The precipitate was filtered off, washed with excess water and air-dried to give 4.9 g of crude product (via NMR, 86% yield). Recrystallization from ethanol afforded a tan solid, m.p. 149°–150° dec.

Analysis: Calc. for $C_{12}H_{10}ClNO_3S$: C: 50.79; H: 3.53; N: 4.94. Found: C: 50.77; H: 3.53; N: 4.82.

EXAMPLE 2

2-[alpha-(2,5-Dimethylphenyl)-2-chloromethyl sulfonyl] pyridine-1-oxide

Carbon tetrachloride (3.40 g, 22 mmol) and powdered sodium hydroxide (1.0 g, 25 mmol) were placed in 20 ml of dimethylformamide. The mixture was allowed to cool to 0° C. in an acetone-ice bath, whereupon 2-(2,5-Dimethylphenylmethylsulfonyl)pyridine-1-oxide (5.54 g, 20 mmol) was added in one portion while vigorously stirring the reaction mixture. After 30 min. at 0° C. the mixture was poured into 200 ml of well-stirred water.

The resulting brown precipitate was filtered off, washed with excess water and air-dried to afford 5.0 g crude product (pure via NMR, 62% yield). Recrystallization from ethanol afforded 2.7 g of light tan powder, m.p. 183°–184° dec.

Analysis: Calc. for $C_{14}H_{14}ClNO_3S$: C: 54.02; H: 4.50; N: 4.50. Found: C: 53.53; H: 4.48; N: 4.56.

EXAMPLE 3

2-[alpha-(3,4-Dimethylphenyl)alpha-chloromethyl] pyridine-1-oxide

Carbon tetrachloride (5.4 g, 35 mmol) and freshly ground sodium hydroxide (1.4 g, 35 mmol) were placed in a flask containing 20 ml of dimethylformamide and the mixture cooled to 0° with an acetone-ice bath. While rapidly stirring this mixture, 2-(3,4-Dimethylphenylmethylsulfonyl) pyridine-1-oxide (8.31 g, 30 mmol) was added in one portion.

After 30 min., the reaction mixture was poured into 300 ml of stirred water and the resulting precipitate was separated by filtration. The precipitate was washed with excess water and allowed to air dry, affording 8.78 g of crude product (pure via NMR, 94% yield). Recrystallization from ethanol-chloroform yielded 5.1 g of pure product, m.p. 164° dec.

Analysis: Calc. for $C_{14}H_{14}ClNO_3S$: C: 54.02; H: 4.50; N: 4.50. Found: C: 53.77; H: 4.53; N: 4.51.

EXAMPLE 4

2-[alpha-(1,1'-Biphenyl-4-yl)-alpha-chloromethyl] pyridine-1-oxide

Carbon tetrachloride (1.23 g, 8.0 mmol) and freshly ground sodium hydroxide (0.29 g, 7.2 mmol) were placed in a reaction flask containing 15 ml of dimethylformamide. After cooling the mixture to 0° with an acetone-ice bath, 2-(1,1'-biphenyl-4-yl-methylsulfonyl) pyridine-1-oxide (2.11 g, 6.5 mmol) was added in one portion while vigorously stirring the reaction mixture. After 35 min. the mixture was poured into 250 ml of well-stirred water, whereupon a solid separated out.

The solid was isolated by filtration, washing with excess water, and air-drying. In this manner, 2.13 g of brown solid was obtained (pure product via NMR, 91% yield), m.p. 182°–184° dec.

$^1$H-NMR: δ 7.05 (1H,s,SO$_2$CHClR), δ 7.2–8.4 (13H,m)

EXAMPLE 5

2-[alpha-(2',2'-Dichloro-1'methylcyclopropyl)-chloromethylsulfonyl] pyridine-1-oxide Carbon tetrachloride (1.28 g, 8.3 mmol) and freshly ground sodium hydroxide (0.31 g, 7.6 mmol) were placed in a reaction flask containing 15 ml of dimethylformamide stirring at 0°. To this was added in one portion while applying vigorous stirring, 2-(2',2'-dichloro-1'-methylcyclopropylmethylsulfonyl) pyridine-1-oxide (2.03 g, 6.9 mmol). The reaction temperature was maintained at 0° with an external acetone-ice bath. After 35 min., the mixture was poured into 200 ml of well-stirred water and the precipitate which separated out was filtered off, washed with excess water, and air-dried to afford 2.00 g of brown solid (pure product via NMR, 88% yield), m.p. 188°–189° dec.

$^1$H-NMR: δ 1.72 (3H,s,CH$_3$), δ 1.76 (1H,d,J=8 Hz, 3-H), δ 2.35 (1H,d,J-8 Hz, 3-H, δ 6.20 (1H, s, α-H), δ 7.50 (2H,m. pyridyl), δ8.15 (2H, m, pyridyl).

The foregoing and similar preparations are summarized in Table I.

TABLE I
HERBICIDAL COMPOUNDS

| Compound Number | Name | m.p. | Empirical Formula | Analysis: Calc/Found C | H | N |
|---|---|---|---|---|---|---|
| 2 | 2-[α-(2,5-Dimethylphenyl)-α-chloromethylsulfonyl]pyridine-1-oxide | 183–4° dec | C$_{14}$H$_{14}$ClNO$_3$S | 54.02 / 53.53 | 4.50 / 4.48 | 4.50 / 4.56 |
| 1 | 2-(α-Phenyl-α-chloromethylsulfonyl)pyridine-1-oxide | 149–50° | C$_{12}$H$_{10}$ClNO$_3$S | 50.79 / 50.77 | 3.53 / 3.53 | 4.94 / 4.82 |
| 6 | 2-[α-(2,6-Dichlorophenyl)-α-chloromethylsulfonyl]pyridine-1-oxide | 163–65° dec | C$_{12}$H$_8$Cl$_3$NO$_3$S | 40.87 / 41.00 | 2.29 / 2.24 | 3.97 / 4.08 |
| 7 | 2-[α-(3-Fluorophenyl)-α-chloromethylsulfonyl]pyridine-1-oxide | 160–1° dec | C$_{12}$H$_9$ClFNO$_3$S | 47.77 / 47.65 | 3.01 / 3.13 | 4.64 / 4.58 |
| 12 | 2-[α-(4-Fluorophenyl)-α-chloromethylsulfonyl]pyridine-1-oxide | 166° dec | C$_{12}$H$_9$ClFNO$_3$S | 47.77 / 47.61 | 3.01 / 3.12 | 4.64 / 4.64 |
| 8 | 2-[α-(2-Fluorophenyl)-α-chloromethylsulfonyl]pyridine-1-oxide | 166° dec | C$_{12}$H$_9$ClFNO$_3$S | 47.77 / 47.51 | 3.01 / 3.10 | 4.64 / 4.63 |
| 9 | 2-[α-(4-Methylphenyl)-α-chloromethylsulfonyl]pyridine-1-oxide | 166° dec | C$_{13}$H$_{12}$ClNO$_3$S | 52.44 / 52.44 | 4.06 / 4.06 | 4.70 / 4.69 |
| 10 | 2-[α-(2,4-Dichlorophenyl)-α-chloromethylsulfonyl]pyridine-1-oxide | 174° dec | C$_{12}$H$_8$Cl$_3$NO$_3$S | 40.87 / 40.65 | 2.29 / 2.47 | 3.97 / 4.02 |
| 11 | 2-[α-(2-Ethoxyphenyl)-α-chloromethylsulfonyl]pyridine-1-oxide | 164° dec | C$_{14}$H$_{14}$ClNO$_4$S | 51.30 / 50.85 | 4.31 / 4.36 | 4.27 / 4.29 |
| 13 | 2-[α-(2-Methylphenyl)-α-chloromethylsulfonyl]pyridine-1-oxide | 171–2° dec | C$_{13}$H$_{12}$ClNO$_3$S | 52.52 / 52.29 | 4.04 / 4.09 | 4.71 / 4.55 |
| 14 | 2-[α-(2,4-Dimethylphenyl)-α-chloromethylsulfonyl]pyridine-1-oxide | 169–70° dec | C$_{14}$H$_{14}$ClNO$_3$S | NMR, IR | | |
| 3 | 2-[α-(3,4-Dimethylphenyl)-α-chloromethylsulfonyl]pyridine-1-oxide | 165° dec | C$_{14}$H$_{14}$ClNO$_3$S | 54.02 / 53.77 | 4.50 / 4.53 | 4.50 / 4.51 |
| 15 | 2-[α-(2,4,6-Trimethylphenyl)-α-chloromethylsulfonyl]pyridine-1-oxide | 189–91° dec | C$_{15}$H$_{16}$ClNO$_3$S | NMR, IR | | |
| 16 | 2-[α-(3,4-Dichlorophenyl)-α-chloromethylsulfonyl]pyridine-1-oxide | 155–7° dec | C$_{12}$H$_8$Cl$_3$NO$_3$S | NMR, IR | | |
| 17 | 2-[α-(2-Nitrophenyl)-α-chloromethylsulfonyl]pyridine-1-oxide | 143–5° | C$_{12}$H$_9$ClN$_2$O$_5$S | NMR, IR | | |
| 18 | 2-[α-(2,5-Dimethoxyphenyl)-α-chloromethylsulfonyl]pyridine-1-oxide | 165–6° dec | C$_{14}$H$_{14}$ClNO$_5$S | 48.98 / 48.15 | 4.08 / 4.25 | 4.08 / 4.12 |
| 19 | 2-[α-(2,5-Diisopropylphenyl)-α-chloromethylsulfonyl]pyridine-1-oxide | 160–2° dec | C$_{18}$H$_{22}$ClNO$_3$S | NMR, IR | | |
| 20 | 2-[α-(2-Naphthyl)-α-chloromethylsulfonyl]pyridine-1-oxide | 160–3° dec | C$_{16}$H$_{12}$ClNO$_3$S | NMR, IR | | |
| 21 | 2-[α-(3-Bromophenyl)-α-chloromethylsulfonyl]pyridine-1-oxide | 168–9° dec | C$_{12}$H$_9$BrClNO$_3$S | NMR, IR | | |
| 5 | 2-[α-(2',2'-Dichloro-1'-methylcyclopropyl)-α-chloromethylsulfonyl]pyridine-1-oxide | 188–89° dec | C$_{10}$H$_{10}$Cl$_3$NO$_3$S | NMR, IR | | |
| 22 | 2-[α-(3-Methylphenyl)-α-chloromethylsulfonyl]pyridine-1-oxide | 165° dec | C$_{13}$H$_{12}$ClNO$_3$S | NMR, IR | | |
| 23 | 2-[α-(3-Trifluoromethylphenyl)-α-chloromethylsulfonyl]pyridine-1-oxide | 139–42° dec | C$_{13}$H$_9$ClF$_3$NO$_3$S | NMR, IR | | |
| 24 | 2-[α-(4-Cyanophenyl)-α-chloromethylsulfonyl]pyridine-1-oxide | 189–90° dec | C$_{13}$H$_9$ClN$_2$O$_3$S | NMR, IR | | |
| 25 | 2-[α-(4-Nitrophenyl)-α-chloromethylsulfonyl]pyridine-1-oxide | 191° dec | C$_{12}$H$_9$ClN$_2$O$_5$S | NMR, IR | | |
| 26 | 2-[α-(4-Chlorophenyl)-α-chloromethylsulfonyl]pyridine-1-oxide | 170° dec | C$_{12}$H$_9$Cl$_2$NO$_3$S | NMR, IR | | |
| 27 | 2-[α-(4-t-Butylphenyl)-α-chloromethylsulfonyl]pyridine-1-oxide | 153° dec | C$_{16}$H$_{18}$ClNO$_3$S | NMR, IR | | |
| 4 | 2-[α-(1,1'-Biphenyl-4-yl)-α-chloromethylsulfonyl]pyridine-1-oxide | 182–4° dec | C$_{18}$H$_{14}$ClNO$_3$S | NMR, IR | | |
| 28 | 2-[α-(2,3-Dimethoxyphenyl)-α-chloromethylsulfonyl] | 154–5° | C$_{14}$H$_{14}$ClNO$_5$S | NMR, IR | | |

TABLE I-continued

HERBICIDAL COMPOUNDS

| Compound Number | Name | m.p. | Empirical Formula | Analysis: Calc/Found C H N |
|---|---|---|---|---|
| | pyridine-1-oxide | dec | | |
| 29 | 2-[α-(2,3,6-Trichlorophenyl)-α-chloromethyl-sulfonyl]pyridine-1-oxide | 159-61° dec | $C_{12}H_7Cl_4NO_3S$ | NMR, IR |
| 30 | 2-[α-(2-Iodophenyl)-α-chloromethylsulfonyl]pyridine-1-oxide | 172° dec | $C_{12}H_9ClINO_3S$ | NMR, IR |
| 31 | 2-[α-(2-Phenoxyphenyl)-α-chloromethylsulfonyl]pyridine-1-oxide | 152° dec | $C_{18}H_{14}ClNO_4S$ | NMR, IR |
| 32 | 2-[α-(4-Carboxyphenyl)-α-chloromethylsulfonyl]pyridine-1-oxide | 201° dec | $C_{13}H_{10}ClNO_5S$ | NMR, IR |
| 33 | 2-[α-(4-Methyl-2,3,5,6-tetrachlorophenyl)-α-chloromethylsulfonyl]pyridine-1-oxide | 198-200° dec | $C_{13}H_8Cl_5NO_3S$ | NMR, IR |
| 34 | 2-[α-(4-Isopropylphenyl)-α-chloromethylsulfonyl]pyridine-1-oxide | 152° dec | $C_{15}H_{16}ClNO_3S$ | NMR, IR |
| 35 | 2-[α-(4-Ethylphenyl)-α-chloromethylsulfonyl]pyridine-1-oxide | 132-35° dec | $C_{14}H_{14}ClNO_3S$ | NMR, IR |

The following examples will serve to illustrate the herbicidal method and composition of the invention in more detail. The examples summarized in Table II illustrate control of weeds with the chemicals while Table III illustrates improved crop selectivity.

EXAMPLE 6

To illustrate effectiveness of the described 2-(chloromethylsulfonyl)pyridine 1-oxides as preemergent herbicides, 600 mg chemical is dissolved in 10 ml organic solvent (e.g., acetone) to which 30 mg conventional emulsifying agent (e.g., isoctyl polyethoxyethanol, "Triton X100" (trademark) is added. The solution is diluted to 100 ml with distilled water. Twenty milliliters of this 6000 ppm solution is diluted to 250 ppm with distilled water. The chemical is applied at the rate of 10 lbs/A (pounds per acre) by drenching 46 ml of the 250 ppm solution on the surface of soil in 4½ inch diameter plastic pots which had been sown with the following weed seeds: rough pigweed (*Amaranthus retroflexus* L.), jimsonweed (*Datura stramonium* L.), tall morning glory (*Ipomea purpurea*(L.) Roth), switchgrass (*Panicum virgatum* L.), green foxtail (*Setaria viridis* (L.) Beauv.). The percent control of the weeds compared to untreated checks is determined two weeks after treatment. Table II shows the results with the preemergence herbicides of the invention prepared in accordance with the above examples.

(e.g., isoctyl polyethoxyethanol, "Triton X100" (Trademark) is added. The solution is diluted to 100 ml with distilled water. Forty ml of the resulting 250 ppm solution is diluted to 100 ml with distilled water. The chemical is applied at the rate of 4 lb/A (Pounds per acre) by drenching 80 ml of the 100 ppm on the surface of soil in 6 inch diameter plastic pots which had been sown with weed and crop seeds. The percent control of the weeds and crop injury is determined three weeks after treatment. Table III shows the selectivity advantage of the chloromethyl compounds.

The compounds listed in Table III beginning with No. 36 are as follows 36 2-[1-(2,5-dimethylphenyl) ethylsulfonyl] pyridine-1-oxide
37 2-[1-(2,5-dimethylphenyl) methylsulfonyl]pyridine-1-oxide
38 2-(2,6-dichlorobenzyl) methyl sulfonyl pyridine-1-oxide
39 2-(3'-fluorobenzyl) methyl sulfonyl pyridine-1-oxide
40 2-(2,4-dichlorobenzyl) methyl sulfonyl pyridine-1-oxide
41 2-(2-ethoxyphenyl) methyl sulfonyl pyridine-1-oxide
42 2-(2-fluorobenzyl) methyl sulfonyl pyridine-1-oxide
43 2-[1-(4'-methylphenyl) ethyl sulfonyl]pyridine-1-oxide
44 2-(p-tolylmethyl) methyl sulfonyl pyridine-1-oxide
45 2-(1'-phenyl)ethyl sulfonyl pyridine-1-oxide

TABLE II

Herbicide Activity of 2- (chloromethylsulfonyl)pyridine 1-oxide derivatives.

| Compound No. | Rate lb/A | Pig Weed | Jimson-Weed | Wild Morning Glory | Barnyard Grass | Switch Grass | Green Foxtail | Purple Nutsedge |
|---|---|---|---|---|---|---|---|---|
| 2 | 10 | 100 | 0 | 50 | 98 | 98 | 98 | 100 |
| 1 | 10 | — | — | 100 | 100 | 100 | 98 | 100 |
| 6 | 10 | — | 0 | 0 | 98 | 100 | 100 | 100 |
| 7 | 10 | — | 0 | 0 | 98 | 100 | 95 | 100 |
| 8 | 10 | — | 0 | 0 | 100 | 100 | 98 | 100 |
| 9 | 10 | — | 0 | 0 | 100 | 100 | 98 | 0 |
| 10 | 10 | — | 0 | 0 | 50 | 100 | 75 | 100 |
| 11 | 10 | — | 0 | 0 | 98 | 100 | 98 | 0 |

EXAMPLE 7

Selectivity of a herbicide is desirable since it allows control of weeds growing among desirable crop plants. To illustrate the usefulness of the compounds of this invention as selective preemergence herbicides, 25 mg chemical is dissolved in 5 ml organic solvent (e.g., acetone) to which 10 mg conventional emulsifying agent 46 2-(benzyl) methyl sulfonyl pyridine-1-oxide
All other compounds are as previously listed in Table I.

TABLE III

Crop selectivity of alpha-chloro, alpha-methyl and unsubstituted 2-sulfonyl pyridine 1-oxides

| No. | Rate lb/A | Percent Weed Control or Crop Injury | | | |
|---|---|---|---|---|---|
| | | Barnyard Grass | Switch Grass | Goose Grass | Cucumber |
| 36 | 4 | 100 | 100 | 100 | 80 |
| 37 | 4 | 100 | 100 | 100 | 60 |
| 2 | 4 | 100 | 100 | 100 | 20 |
| 38 | 4 | 100 | 100 | 100 | 95 |
| 6 | 4 | 100 | 100 | 100 | 50 |
| 38 | 2 | 100 | 100 | 100 | 50 |
| 6 | 2 | 95 | 100 | 100 | 0 |
| 39 | 4 | 100 | 50 | 100 | 40 |
| 7 | 4 | 100 | 100 | 100 | 0 |
| 40 | 4 | 100 | 100 | 100 | 25 |
| 10 | 4 | 95 | 100 | 100 | 0 |
| 41 | 4 | 100 | 100 | 100 | 25 |
| 11 | 4 | 95 | 70 | 100 | 0 |
| 42 | 4 | 100 | 100 | 100 | 0 |
| 8 | 4 | 90 | 100 | 100 | 0 |
| 43 | 4 | 100 | 100 | 100 | 30 |
| 44 | 4 | 100 | 100 | 100 | 0 |
| 9 | 4 | 85 | 100 | 100 | 0 |
| 45 | 4 | 100 | 100 | 100 | 25 |
| 46 | 4 | 95 | 85 | 100 | 0 |
| 1 | 4 | 100 | 100 | 100 | 0 |

EXAMPLE 8

Listed below are non-limiting examples of formulations which can be used in this invention.

| | |
|---|---|
| 1. 9.6% active one lb/gallon emulsifiable concentrate | |
|   a. 2-(α-2,5-Dimethylphenyl-α-chloromethylsulfonyl)pyridine 1-oxide | 0.6 gm |
|   b. Blend of oil soluble sulfonates with polyoxyethylene ethers (Emcol N39-BU (Trademark) Witco Chemical Corp.; e.g., nonylphenol polyoxyethylene plus calcium dodecylbenzene sulfonate) | 0.55 gm |
|   c. Chloroform | 2.4 gm |
|   d. Benzaldehyde | 2.7 gm |
| 2. 75% active wettable powder | |
|   a. 2-(α-2,5-Dimethylphenyl-α-chloromethyl sulfonyl) pyridine 1-oxide | 78.3 gm |
|   b. Sodium N—methyl-N Palmitoyl laurate (Igepon TN-74 (trademark) GAF Corp.) | 0.5 gm |
|   c. Sodium alylnapthalene sulfonate (Nekal BA-77 (Trademark) GAF Corp.) | 1.0 gm |
|   d. Sodium salt of sulfonated kraft Lignin (0.5 mole) Polyfon H (Trademark) Westvaco) | 1.0 gm |
|   e. Alkaryl Polyether alcohol OPE 9-10 on an inert carrier (40% active) (Triton AG-120 (Trademark) Rohm and Haas. | 1.0 gm |
|   f. Hydrated amorphous silica (Hi Sil 233 (Trademark) | 7.3 gm |
|   g. Kaolinite clay (Dixie Clay) (Trademark) | 10.9 gm |
| 3. 5% active granule | |
|   a. 2-(α-2,5-Dimethylphenyl-α-chloromethylsulfonyl) pyridine 1-oxide | 1.0 gm |
|   b. Methyl chloride | 9.0 gm |
|   c. Above solution sprayed onto hydrated magnesium aluminum Silicate 25/50 mesh (Attaclay) (Trademark) | 19.0 gm |

What is claimed is:

1. A compound of the formula

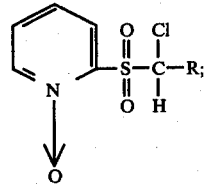

wherein

R is selected from the group consisting of: phenyl; phenyl substituted with one of the substituents $C_1$ to $C_8$ alkyl, $C_1$ to $C_8$ alkoxy, phenoxy, halogen, trifluoromethyl, trichloromethyl, or nitro; 2-naphthyl; and 2-(2',2'-dichloro-1'-methylcyclopropyl).

2. A compound as in claim 1 wherein R is phenyl.

3. A compound as in claim 1 wherein R is substituted phenyl.

4. A compound as in claim 1 wherein R is 2-naphthyl.

5. A compound as in claim 1 wherein R is 2-(2',2'-dichloro-1'-methylcyclopropyl).

6. A compound as in claim 1 wherein R is 2,5-dimethylphenyl.

7. A compound as in claim 1 wherein R is 2,6-dichlorophenyl.

8. A compound as in claim 1 wherein R is 3-fluorophenyl.

9. A compound as in claim 1 wherein R is 2-fluorophenyl.

10. A compound as in claim 1 wherein R is 4-methylphenyl.

11. A compound as in claim 1 wherein R is 2,4-dichlorophenyl.

12. A compound as in claim 1 wherein R is 2-ethoxyphenyl.

* * * * *